United States Patent [19]

Norell

[11] Patent Number: 4,973,047
[45] Date of Patent: Nov. 27, 1990

[54] THERAPEUTIC DEVICE FOR LUNG EXERCISE

[76] Inventor: Erik Norell, Vavaregatan 5 B, S-531 34 Lidköping, Sweden

[21] Appl. No.: 446,353

[22] Filed: Dec. 5, 1989

[30] Foreign Application Priority Data

Dec. 9, 1988 [EP] European Pat. Off. ............ 88850416

[51] Int. Cl.⁵ .............................................. A63B 23/18
[52] U.S. Cl. ....................................... 272/99; 128/727
[58] Field of Search ................. 272/99, 130; 128/720, 128/725, 727; 73/239

[56] References Cited

U.S. PATENT DOCUMENTS

| | | | |
|---|---|---|---|
| 3,822,699 | 7/1974 | Cleary | 128/727 |
| 4,025,070 | 5/1977 | McGill et al. | 128/727 X |
| 4,221,381 | 9/1980 | Ericson | 272/99 |
| 4,291,787 | 9/1981 | Brentham | 272/130 X |
| 4,533,137 | 8/1985 | Sonne | 128/725 X |
| 4,601,465 | 7/1986 | Roy | 272/99 |
| 4,634,117 | 1/1987 | Kramer | 272/99 |
| 4,739,987 | 4/1988 | Nicholson | 272/99 |

FOREIGN PATENT DOCUMENTS 2379291 10/1978 France ................................. 272/99

Primary Examiner—Robert Bahr
Attorney, Agent, or Firm—Sughrue, Mion, Zinn, Macpeak and Seas

[57] ABSTRACT

A therapeutic device for exercising and stimulating the lung with the aid of a mouthpiece (1) which sealingly co-acts with the lips of the user during the exhalation phase of a breathing cycle. The mouthpiece is connected to a cylindrical, hollow extension (2) and communicates with the surrounding atmosphere through an opening (3) of adjustable area disposed in the extension. The opening (3) is located in the circumference of the extension (2) and the extension is closed-off with the aid of a sealing plug having the function of a valve (4). The valve is rotatable and has a surface which co-acts with the inner surface of the extension, such that the exposed area of the opening (3) can be adjusted by rotation of the valve. To facilitate adjustment of the exposed area of the opening, the valve (4) and the extension (2) are provided with respective, mutually co-acting promontories and recesses which are effective in releasably fixing the valve in relation to the extension in a desired rotational position selected from a number of relative rotational positions, by rotation of the valve relative to the extension. This enables the device to be readily adjusted to a pre-determined exhalation resistance.

10 Claims, 3 Drawing Sheets

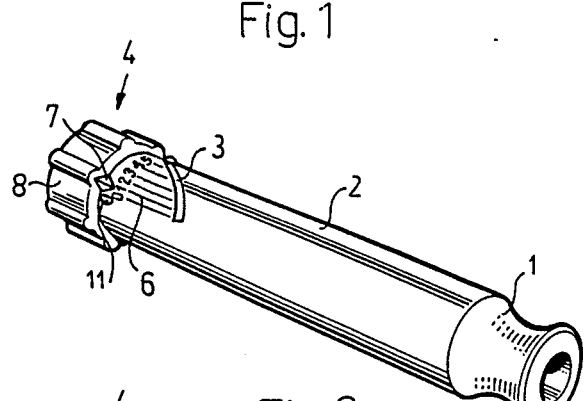
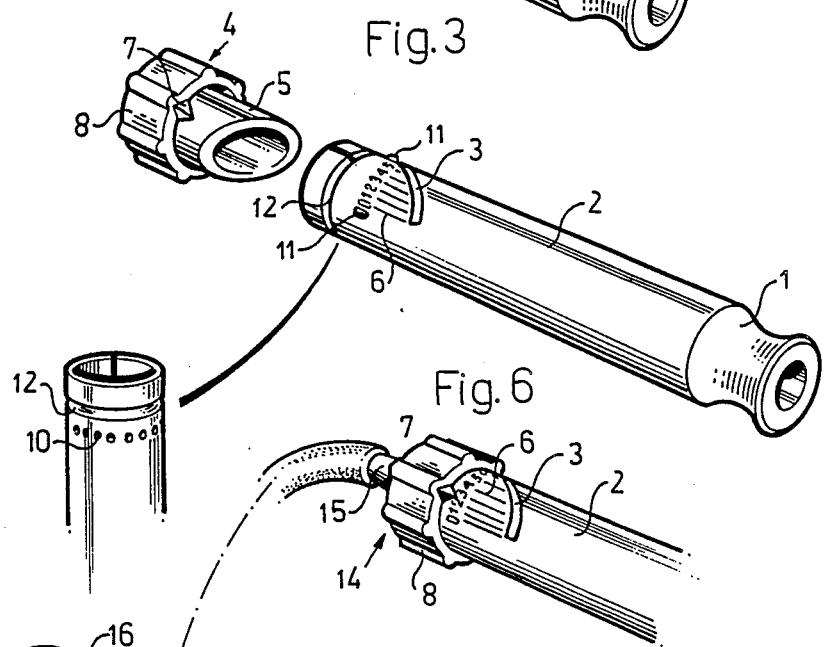
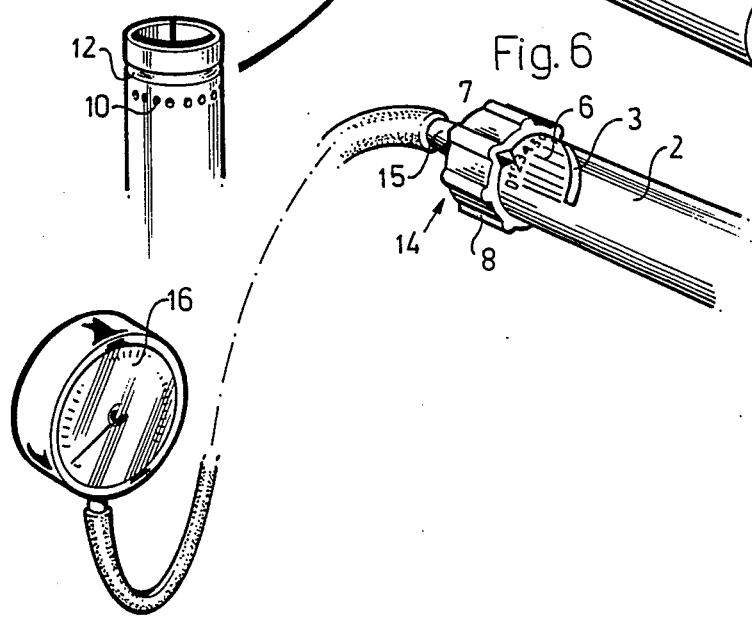

THERAPEUTIC DEVICE FOR LUNG EXERCISE

BACKGROUND OF THE INVENTION

The present invention relates to a therapeutic device, and more particularly to a lung exercising and lung stimulating device of the kind comprising a mouthpiece which coacts sealingly with the lips of the user during the exhaling phase of a breathing cycle and which is joined to a hollow cylindrical extension and communicates with the surrounding atmosphere through an opening of adjustable area provided in the extension.

It is known that respiratory organs can be exercised and stimulated by exhaling against a given resistance. This will cause the air passages in the lungs to dilate and therewith promote the natural ability of the body to transport phlegm, mucus and liquid output from the lungs. This method of treatment is particularly effective in the treatment of asthma, and is also used with patients who have undergone heart surgery, and in certain instances with patients who have suffered traffic injuries.

The treatment is applied with the aid of breathing masks which have been designed particularly for the purpose intended and which are provided with a check valve which while allowing air to be inhaled freely is closed against the expiration air, this air being forced to pass through a small opening of limited area located in the expiration channel in the mouthpiece, thereby providing the requisite resistance to the expiration air.

Because such masks are relatively expansive to produce, they are only found in comparatively small numbers. Furthermore, it is necessary to adapt the resistance offered against exhalation to the requirements of different individuals, or to change the nozzle in the exhalation passage of such masks during the course of treatment of an individual. The masks are also relatively difficult to clean and disinfect, and cannot be carried easily by the patient for use at regular intervals during, e.g., a normal working day.

Instead of masks, the aforedescribed method of treatment is normally effected with a bottle which is filled partially with water and into which there is inserted a plastic hose through which the patient exhales. The resistance to exhalation is determined by the level of the water in the bottle. Although this device is inexpensive, the treatment is normally given by a physiotherapist, who needs to spend relatively long periods of time in adapting the water level in the bottle to the patient's requirement. A patient will normally be expected to exhale into the bottle at least 30 times in close succession at least from 4 to 10 times each day. The use of a water-filled bottle also has other drawbacks and limitations. Among other things, it cannot be carried about ones person on all occasions.

SUMMARY OF THE INVENTION

The main object of the invention is therefore to provide a less expensive, simpler and more manageable device for exercising and stimulating the respiratory organs of an individual, and also a device which can be readily carried on ones person and used in different situations, even while being engaged in other activities.

Accordingly, a therapeutic device of the kind described in the opening paragraph of this specification is characterized particularly in that said opening is disposed in the circumference of the extension; in that the extension is closed-off with the aid of the rotatable end plug which has the function of a valve and has a surface which coacts with the inner surface of the extension such that rotation of the plug will adjust the free or exposed area of said opening; and in that the plug, or valve, and the extension are provided with respective mutually coacting promontories and recesses which when rotating the plug relative to the extension releasably fires them in relation to one another in a selected one of a number of relative rotational positions, for setting a device to a pre-determined exhalation resistance.

Such a device can be carried easily in a pocket, a handbag or the like, and can be readily set to the resistance prescribed by the patient's doctor. Because the device can be adjusted to the desired setting in a stepwise fashion, it can be used correctly by people with poor vision and also by people whose hands tremble or shake.

In the case of a preferred embodiment, the opening has the form of an elongated slot disposed in the circumference of the extension. The slot extends obliquely in relation to the longitudinal axis of the extension and the surface of the plug or valve coacting with the opening is bounded by an edge which forms substantially a right angle with the slot. This will enable the exposed or free area of the slot to be adjusted more accurately, since complete closure of the slot will require greater rotational movement than that required if the slot were to extend fully tangentially.

The valve, or plug, will preferably include a collar-like part which extends across the end part of the extension, and the aforesaid promontories and recesses will be disposed on the mutually facing surfaces of said collar and said end part. In this case, the surface of the valve coacting with the inner surface of the extension will comprise an outwardly projecting part of a cylindrical valve part projecting into the extension, said extension end part being received in a circular groove disposed between the collar part of the valve and said cylindrical part thereof. This provides an extremely effective guide means and will enable the valve to be rotated readily relative to the extension.

Preferably, the valve and the extension will be provided with mutually coacting scale markings which indicate the free area of the opening to which the device has been set, and the device will include stop means effective in restricting rotation of the valve to the region between a totally exposed opening and a totally closed opening.

The extension and the valve will preferably be provided with a circumferentially extending groove and a bead coacting therewith, so as to enable thhe extension and the valve to be readily snapped together.

In order to enable the device to be calibrated and a patient to be tested or a suitable slot opening to be prescribed, the valve may be provided with means for connecting the interior of the extension to a pressure indicating device, such as a manometer.

Since some patients may find it difficult to hold the device between their lips while exhaling forcibly into the mouthpiece, the mouthpiece is suitably adapted to be sealingly and detachably connected to a biting nozzle of suitable configuration. This biting nozzle may conveniently be provided with an internally located bead intended for coaction with a concave part of the mouthpiece, such as to form a detachable snap connection.

BRIEF DESCRIPTION OF THE DRAWINGS

The invention will now be described in more detail with reference to exemplifying embodiments thereof illustrated in the accompanying drawings, in which FIG. 1 is a perspective view of a device constructed in accordance with the invention;

FIG. 3 is an exploded view of the device;

FIG. 6 illustrates an alternative embodiment of the valve means; and

DETAILED DESCRIPTION OF THE PREFERRED EMBODIMENT

Figure 2:
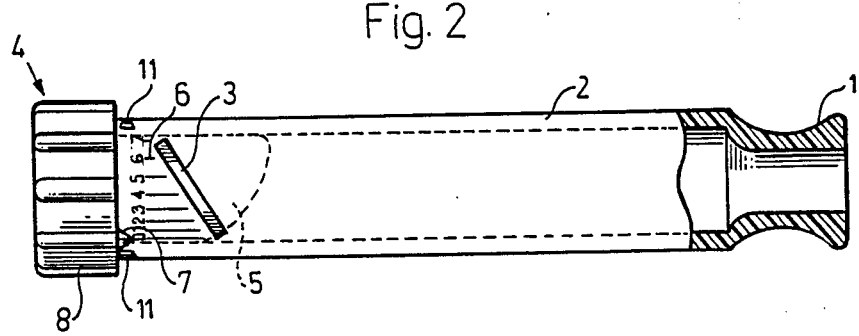
FIG. 2 is a side view of the device, shown partly in section.

The device illustrated in FIGS. 1-3 includes a mouthpiece 1 which merges with a cylindrical, hollow extension 2. Disposed in the circumference of the extension 2 is an elongated slot 3, which forms an angle with the longitudinal axis of the extension. The free end of the extension is closed by means of an end plug 4, which has the function of a valve.

The end plug 4 includes a cylindrical part 5 which is a close fit in the cylindrical extension 2 and which has a bevelled end surface. As will best be seen from FIG. 2 and the section view of FIG. 4, this bevelled end of the cylindrical part 5 co-acts with the slot-like opening 3 upon rotation of the plug 4, such as to adjust the exposed area of the slot opening. Thus, when using the inventive device, the resistance to exhalation can be readily adjusted by rotating the plug 4 in relation to the cylindrical extension 2. Air is breathed in along the outer surfaces of the mouthpiece.

Figure 4:
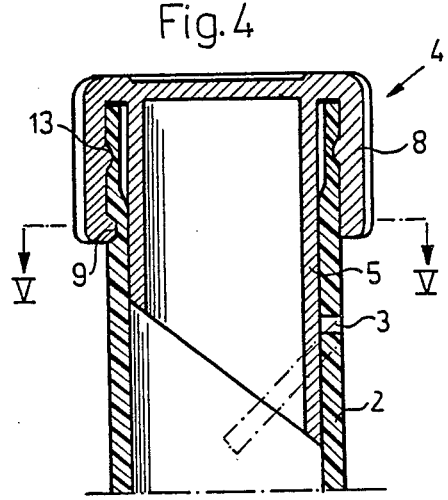
FIG. 4 is a longitudinal section view of the outer end of the device.

As illustrated in FIG. 4, the end surface of the cyclindrical part 5 extends substantially at right angles to the slot-like opening 3, so as to enable accurate adjustments to be made to the exposed area of the slot. As a result of this arrangement, a relatively large rotary movement of the plug 4 is required to adjust the slot opening between a fully open slot and a fully closed slot, which facilitates fine adjustments of the exposed slot area.

In order to enable the device to be set to an exhalation resistance prescribed by a doctor, the cylindrical extension 2 is also provided with a scale 6 and the plug 4 with an indicator 7 which passes over the scale. The device is also constructed in a manner which enables it to be set to different, fixed positions, such as to enable the device to be set to precisely the desired exhalation resistance and such that mutually the same resistances can be re-set at different occasions during a course of treatment and such as to enable blind or partially sighted individuals or individuals whose hands tremble or shake or have reduced mobility or sensitivity to use the instrument without undue difficulty.

Figure 5:
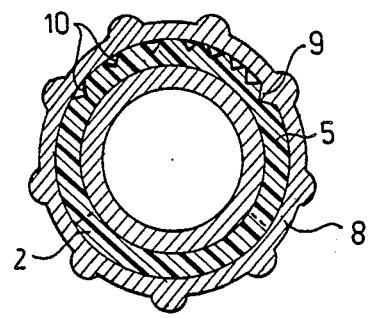
FIG. 5 is a cross-sectional view taken on the line V—V in FIG. 4.

To this end, the end plug 4 of the illustrated embodiment is provided with a collar-like part 8 which surrounds the end part of the cylindrical extension 2 and which can be readily gripped with the fingers. Arranged on the inner surface of the collar-like part 8 is at least one promontory 9, which is intended to co-act with different recesses or indents 10 disposed on the opposing part of the extension circumference, as shown more clearly in the separate illustration of FIG. 3 and in FIGS. 4 and 5.

Thus, when the plug 4 is rotated, it can be snapped into the various, pre-determined positions through the co-action between said promontory 9 and indents 10. The reference 11 identifies two stop members which co-act with the indicator 7, such as to limit the rotational movements of the plug 4. When the device is used by a blind person, the device can be set to the prescribed exhalation resistance by turning the plug to one terminal position and then rotating the plug 4 while counting the number of readily discernible "snaps" effected by the plug during its rotation.

For the purpose of facilitating dismantling of the device for cleaning purposes, and for faciliting subsequent assembly of the device and for enabling the end plug 4 to be readily rotated, the plug is attached to the cylindrical extension 2 with the aid of a snap connector comprising a groove 12 which extends circumferentially around the end part of thhe extension 2, and a corresponding bead 13 provided on the inner surface of the collar-like member 8. The entire deive is preferably made of a plastics material, therewith enabling the device to be manufactured cheaply and rationally and also to be cleaned without difficulty.

As illustrated in FIG. 6, the end plug 14 may be provided with means 15 for connecting the device to a manometer 16, thereby enabling the device to be used when prescribing a suitable exhalation resistance or for checking the resistance offered by the device. In this repect, the pressure during exhalation, and therewith the resistance, can be read-off directly on the manometer. Such a manometer connection can also be used when instructing a patient in the speed at which he/she should breathe out. The manometer can also be replaced with some other means, for example a means which will produce an acoustic signal at a given pressure or different acoustic signals in response to variations in pressure levels. Means may also be used which, for instance, change colour or move in response to pressure, so as to render the device more interesting to children.

Older people may find it difficult to hold the device firmly between the lips while at the same time exhaling forcibly through the mouthpiece. In this case, the mouthpiece may be supplemented with a bite nozzle of suitable configuration, as illustrated in FIGS. 7 and 8, capable of being fitted to the standard mouthpiece with the aid of mutually co-acting and mutually sealing snap connectors.

Figure 7:
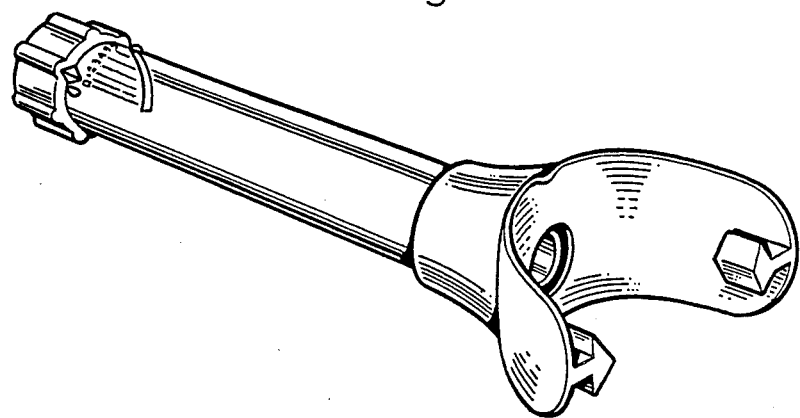
FIGS. 7 and 8 illustrate respectively two embodiments of biting nozzles capable of being connected to the inventive device.
Figure 8:
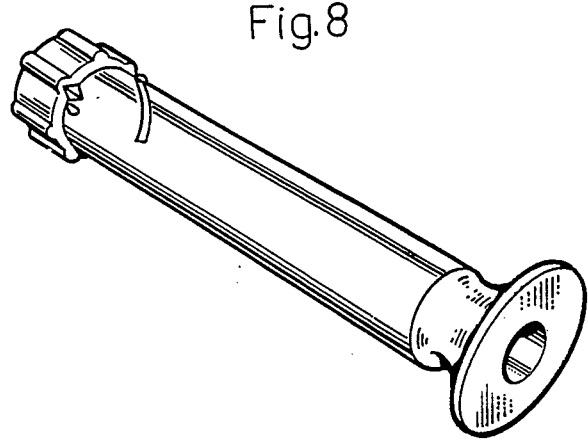

FIG. 8 illustrates an embodiment of a mouthpiece whose width and shape enable it to be held firmly with the aid of the lips and optionally also the teeth, while FIG. 7 illustrates a mouthpiece of essentially the same configuration used by forgmen and like underwater divers, this embodiment further simplifying firm holding of the device, since the teeth are actively used with this embodiment.

The invention is not restricted to the aforedescribed embodiments, and modification can be made within the scope of the following claims, inter alia with respect to the configuration of the various components of the device. For instance, the elongated slot can be replaced with a row of holes and the mutually co-acting promontories and recesses effective in providing the aforesaid snap connection can alternatively be arranged on the inner surface of the extension and the outer surface of the cylindrical part projecting therein.

I claim:

1. A therapeutic device for exercising and stimulating the lungs, comprising: a mouthpiece which co-acts sealingly with the lips of the user during the exhaling phase of a breathing cycle, and a hollow cylindrical extension joined to the mouthpiece and communicating with the surrounding atmosphere through an opening of adjustable area provided in the extension, wherein the opening is disposed in the circumference of the extension; the extension is closed-off wtih a valve comprising a sealing, rotatable end plug provided with a surface intended for co-action with the inner surface of the extension and which, when rotated, exposes a desired area of the opening: and the valve and the extension are provided with respective, mutually co-acting promontories and recesses which upon rotation of the valve in relation to the extension releasably fixate said valve and said extension relative to one another in one desired rotational position of a number of relative rotational positions so as to set the device to a predetermined exhalation resistance.

2. A therapeutic device according to claim 1, wherein the opening is an elongated slot in the circumference of the extension; the slot extends obliquely in relation to the longitudinal axis of the extension; and the valve surface co-acting with the opening is bounded by an edge which extends substantially at right angles to the slot.

3. A therapeutic device according to claim 1, wherein the valve has a collar-shaped part which extends over the end part of the extension; and said promontories and said recesses are dispoed on repsective opposing surfaces of the collar-shaped part and said end part.

4. A therapeutic device according to claim 3, wherein the valve surface co-acting with the inner surface of the extension comprises an outwardly projecting part of a cylindrical part of the valve projecting into the extension; and the extension end part is received in a circular groove located between the collar shaped part of the valve and the cylindrical part of said valve.

5. A therapeutic device according to claim 1, wherein the valve and the extension are provided with mutually co-acting scale indications for indicating the exposed area of said opening.

6. A therapeutic device according to claim 1, wherein said device includes stop members for limiting rotary movement of the valve between a first terminal position in which the opening is fully exposed and a second terminal position in which the opening is fully closed.

7. A therapeutic device according to claim 1, wherein the extension and the valve are respectively provided with a circumferential groove and a bead which is intended to co-act with the groove to form a detachable snap connection.

8. A therapeutic device according to claim 1, further comprising a fitting on the valve for connecting the interior of the extension to a pressure indicating device.

9. A therapeutic device according to claim 1, further comprising a bite nozzle which is sealingly and detachably connected to the mouthpiece.

10. A therapeutic device according to claim 9, wherein the bit nozzle has an inner bead which is intended to co-act with a concave part of the mouthpiece in a manner to form a detachable snap connection.

* * * * *